United States Patent [19]

Hahn et al.

[11] Patent Number: 4,756,597
[45] Date of Patent: Jul. 12, 1988

[54] LIGHT GUIDE, IN PARTICULAR FOR MEDICAL INSTRUMENTS

[75] Inventors: Andreas Hahn, Sauerlach; Alfons Rottmann, Grafing, both of Fed. Rep. of Germany

[73] Assignee: Messerschmitt-Bölkow-Blohm GmbH, Munich, Fed. Rep. of Germany

[21] Appl. No.: 922,200

[22] Filed: Oct. 23, 1986

[30] Foreign Application Priority Data

Nov. 8, 1985 [DE] Fed. Rep. of Germany ....... 3539638

[51] Int. Cl.⁴ ............................................. G02B 23/26
[52] U.S. Cl. ................... 350/96.26; 350/96.10; 128/303.10
[58] Field of Search ............... 350/96.10, 96.20, 96.21, 350/96.26; 128/303.10, 303.15

[56] References Cited

U.S. PATENT DOCUMENTS

| 4,181,397 | 1/1980 | Baker et al. | 350/96.20 |
| 4,253,729 | 3/1981 | Rocton | 350/96.20 |
| 4,422,716 | 12/1983 | Morimoto et al. | 350/96.21 |
| 4,537,193 | 8/1985 | Tanner | 350/96.20 X |
| 4,673,242 | 6/1987 | Logan et al. | 350/96.20 |

FOREIGN PATENT DOCUMENTS

| 0148544 | 11/1979 | Japan | 350/96.21 |
| 0049910 | 3/1982 | Japan | 350/96.20 |
| 0109914 | 7/1982 | Japan | 350/96.20 |
| 0062606 | 4/1983 | Japan | 350/96.20 |

Primary Examiner—Eugene R. LaRoche
Assistant Examiner—Seung Ham
Attorney, Agent, or Firm—Kenyon & Kenyon

[57] ABSTRACT

A light guide, particularly for medical instruments with a light guide fiber, which is surrounded, if needed, by a protective jacket, a sleeve which surrounds the light guide fiber at a distance therefrom and consists of one or several tubes and a feeding unit on one side of the light guide for the feeding of light radiation into the light guide fiber. The light guide fiber and a tube of the sleeve are mounted in the feeding unit, while the other end of the light guide fiber is mounted in the tube of the sleeve. A length compensating element that can change its length axially but is largely not expandable radially, is set in the sleeve to prevent stresses acting longitudinally on the sleeve and light guide fiber due to bending, especially during the coiling of the light guide fiber.

6 Claims, 3 Drawing Sheets

LIGHT GUIDE, IN PARTICULAR FOR MEDICAL INSTRUMENTS

BACKGROUND OF THE INVENTION

The present invention relates to a light guide and in particular, a light guide for medical instruments.

Light guides are used in medicine, e.g. for instruments for laser operations or for endoscopes. In this case, the light guide consists of a feeding unit, a light guide fiber and a casing tube surrounding the fiber at a distance. The light guide fiber itself consists of the light guide core, e.g. of quartz glass, a silicone layer around tne light guide core and a polytetrafluoroethylene jacket.

The feeding unit is used to feed the light or laser radiation focused into the light guide fiber. The light guide fiber and casing tube are mounted in the feeding unit for this purpose. At the other end of the light guide, the light guide fiber is mounted directly in the casing tube.

The casing tube construction varies, depending on the intended application. For example, it may be a relatively thin, flexible, gas- or liquid-tight tube through which gas or liquid is fed by the feeding unit to the front end of the light guide fiber and which cools this end. Such light guides are suitable for use in flexible or rigid instruments.

Relatively rigid and voluminous casing tubes are also known, which consist, if needed, of several tubes, e.g. a gas-tight tube and a protective tube with a relatively thick wall surrounding the former. This protective tube system serves as protection against breaking or damage for the light guide, which is exposed or built into a rigid instrument. Gas and liquid protection is generally not required for the outer protective tube.

When the light guide is bent, stresses build up between the individual parts of the light guide, which cause tensile forces in the longitudinal direction toward the light guide fiber and its light guide core, which is longitudinally rigid. Especially when the light guide, which is up to three meters long, is rolled up for transporting or for other non-use, these stresses can become so great, due to the different radii of casing tube or casing tube system and light guide fiber with light guide core, that the light guide fiber or the light guide core is shifted in one of the mounting sites. When this occurs at the mounting site within the current feeding unit, the focusing of the light radiation to be fed is disturbed. The light guide fiber or the light guide core can be thermally damaged as well. If the light guide fiber or the light guide core shifts at the other mounting site, the light guide fiber or the light guide core can easily be damaged there. When the light guide core is also cooled with gas or liquid, the cooling is weakened by the shift, the light guide core becomes excessively hot and possibly useless.

One could think of mounting the light guide fiber with the light guide core with greater force, to prevent the longitudinal shifting of the light guide core. But this is possible only to a limited extent, if the optical properties of the light guide fiber are not to be impaired by the pressure. For example, the soft silicone layer inserted between light guide core and polytetrafluoroethylene jacket should not be damaged, since this serves as a light refractive barrier layer for the light rays within the light guide core. This alone makes an increase in the mounting force at will impossible.

SUMMARY OF THE INVENTION

The invention is based on the objective of developing a light guide of the type mentioned above in which the axial stresses occurring during the bending of the light guide between individual longitudinally extending elements of the light guide are reduced in a simple manner.

The above and other objects of the present invention are achieved by a light guide, particularly for a medical instrument, having a light guide fiber, a casing that surrounds the light guide fiber at a distance therefrom and comprises at least a casing tube and a feeding unit at one end of the light guide for feeding light radiation into the light guide fiber, with one end of the light guide fiber and the casing tube mounted in the feeding unit and the other end of the light guide fiber mounted in the casing tube, further comprising length compensating means, which can change its length axially, but is largely not expandable radially, inserted into the casing tube for compensating for differences in length of said light guide fiber and casing tube.

By inserting a length compensating means in the casing tube of the light guide, the change in the length of the casing tube or of several protective tubes normally occurring as the light guide is bent, is equalized with regard to the light guide core, and a force acting longitudinally on the light guide fiber and the light guide core is prevented. But this also prevents the danger of shifting the light guide fiber or the light guide core at the mountings or of their piercing through the surrounding jacket.

Conceivable as a length compensating element is an elastic tube, e.g., of silicone, which is a few centimeters long and is connected with the casing tube as part of it, within the feeding unit. It is surrounded by a small spiral spring that undergoes also axial changes in length, but prevents radial bulging, to prevent the radial expansion of this elastic tube, e.g. during the feeding of gas through the casing tube, which would again exert tensile stresses on the light guide fiber.

Corrugated hoses of metal or plastic can also be provided as the length compensating element, and in the latter case, the plastic can be reinforced with threads or fabric to prevent a radial stretching or bulging of the corrugated hose.

The given practical examples for a length compensating element can be used in combination with casing tubes, which must be impervious to gas or liquids. When this requirement does not exist, e.g. in the case of the tubes protecting against mechanical damage of the light guide mentioned above, a telescope piece can be integrated into the protective tube as the length compensating element, in which the protective tube is held movable in the longitudinal direction. This telescope length is again preferably located in the area of the feeding unit.

BRIEF DESCRIPTION OF THE DRAWINGS

The invention will now be explained in more detail in the following detailed description with reference to the drawings, in which.

DETAILED DESCRIPTION

Figure 1:
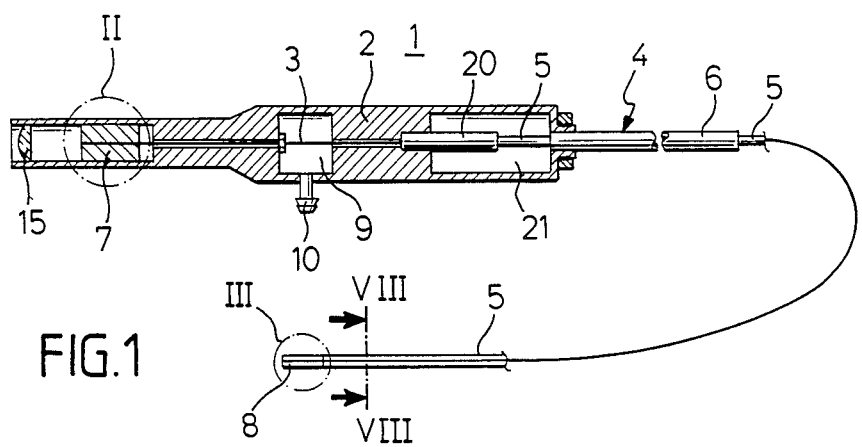
FIG. 1 shows a light guide with a feeding unit, a light guide fiber and a casing tube as well as a length compensating element according to the invention.

A light guide 1 shown in FIG. 1 has a feeding unit 2, a light guide fiber 3 and a casing 4 comprising an inner casing tube 5 and an outer casing tube 6. The inner casing tube 5 extends over the entire length of the light guide fiber and serves as a gas tube. The outer casing tube 6 extends only over part of the length of the light guide fiber and serves mainly to protect against buckling or other mechanical damage.

Figure 2:
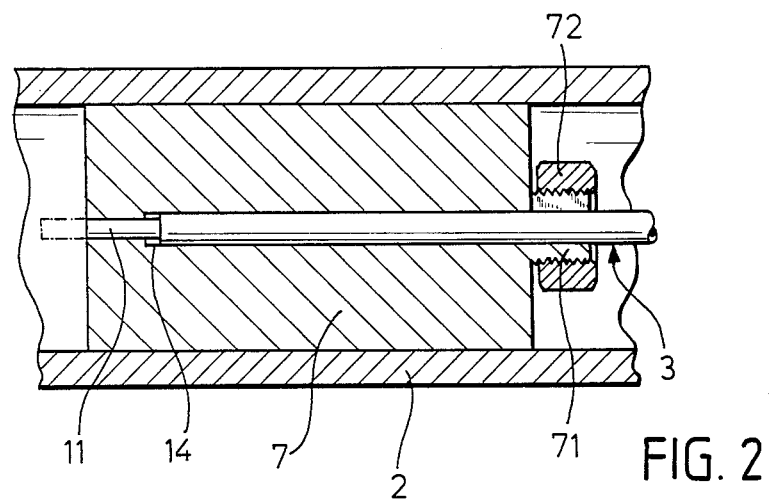
FIGS. 2 and 3 respectively show a sectional view of the light guide at the mounting sites of the light guide fiber in the feeding unit or in the casing tube.

As shown in more detail in FIG. 2, the light guide fiber 3 is mounted within the feeding unit 2 in a fastening block 7 with the aid of a spreading sleeve 71 surrounding light guide fiber 3, and a fixing cap nut 72. At the other end of the light guide fiber 3, which is approximately three meters long, the fiber is mounted, as shown in more detail in FIG. 3, with the aid of a distance piece 8 in the gas tube 5. Gas tube 5 connects with a gas space 9 within feeding unit 2 and is glued together in this area with the housing of feeding unit 2. The gas space has an external connection 10, through which a cooling gas can be fed into gas space 9 and from there into gas tube 5. This gas is used to cool the tip of light guide fiber 3 within distance piece 8, as described in more detail below.

Figure 8:
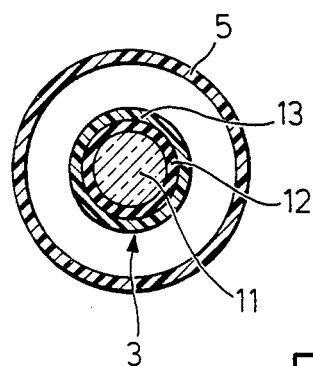
FIG. 8 shows a schematic cross-section along line VIII—VIII in FIG. 1, through a light guide fiber with casing tube.

FIG. 8 shows the structure of the light guide fiber 3, which is constructed of a light guide core 11 made of quartz glass with a diameter of 600$\mu$, a soft silicone layer 12 applied to it with a thickness of 50 to 100$\mu$, and a relatively hard polytetrafluoroethylene jacket 13 surrounding the former with a jacket thickness of approximately 200$\mu$. Light guide fiber 3 is mounted in fastening block 7 in a stepped bore 14, the partial bore of which with its larger diameter accepts the entire light guide fiber 3 with silicone layer 12 and jacket 13, while only the light guide core 11 without the silicone layer and jacket is inserted into the short, front partial bore. In this position the front part of light guide core 11 ends with the front of fastening block 7. In the front of light guide core 11, a focusing lens 15 at the front end of feeding unit 2 is used to feed laser radiation into light guide fiber 3.

On the other side, light guide fiber 3 is also held in a stepped bore 16 in distance piece 8. Distance piece 8 is shaped in the form of a spreading sleeve with longitudinal slits 17, in the partial bore with the larger diameter and surrounds the light guide fiber together with jacket 13. As casing tube 5 is slid into place over the spreading sleeve, light guide fiber 3 is mounted. Light guide core 11, from which the silicone layer and jacket have been removed, is situated in the front partial bore with the smaller diameter. This front partial bore surrounds light guide core 11 at a distance so that gas transported through casing tube 5 is led through longitudinal slits 17 into the front bore, where it cools the exposed end of light guide core 11.

Figure 3:
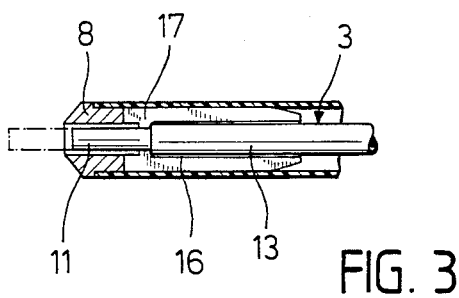

Light guide core 11 can be pressed out of distance piece 8 or fastening block 7 during sharp bending or winding of light guide fiber 3, as is shown in FIGS. 2 and 3 by broken lines. A length compensating element 20, which has a variable length but cannot be stretched radially, is provided in feeding unit 2 for casing tube 5, to prevent this occurrence.

Figure 4:
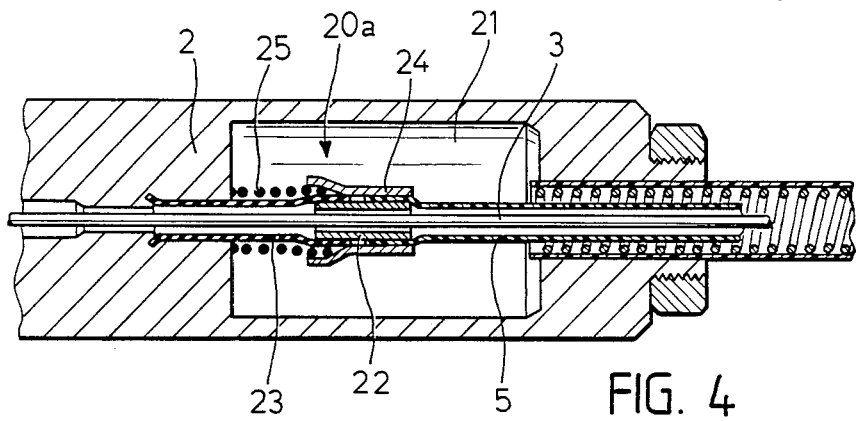
FIGS. 4, 5 and 6 respectively show various practical examples of a length compensating element according to the invention for a gas-tight casing tube.

A practical example of the length compensating element is shown in FIG. 4 and marked 20$a$ in its entirety. This length compensating element 20$a$ is located in a hollow space 21 in the back part of feeding unit 2. Inner casing tube 5 ends in this hollow space and is fastened to a sleeve 22 surrounding light guide fiber 3 at a distance, where it is glued on. An elastic silicone tube 23, which in turn is attached in feeding unit 2, is fastened to the other side of the sleeve. This silicone tube 23 thus forms practically the final section of inner casing tube 5.

In the area of sleeve 22, a metal sleeve 24 is pressed on the two tubes 5 and 23, which is widened in the area of the elastic silicone tube 23. Between the housing of feeding unit 2 and this widened area a spiral spring 25 is located that surrounds elastic silicone tube 23 tightly. Spiral spring 25 is soldered or otherwise attached at its one side to the housing of feeding unit 2. Spiral spring 25 is wound in such a way at rest that it can be elongated as well as shortened. The spiral spring prevents a radial expansion of the elastic silicone tube, when the gas for the cooling of the light guide fiber is fed through this tube. When changes in length take place between casing tube 5 and the light guide fiber during sharp bending or winding of the light guide fiber, these are compensated by length compensating element 20$a$. Consequently, tensile forces do not act on the light guide fiber.

Figure 5:
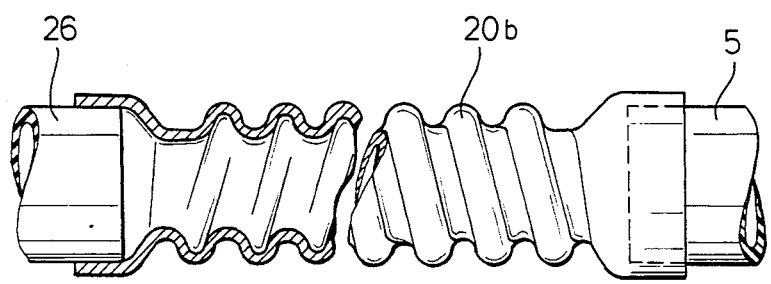

FIG. 5 shows an additional practical example of a length compensating element, which is marked 20$b$. This length compensating element consists of a corrugated metal tube, which takes over the functions of the elastic silicone tube 23 and spiral spring 25 mentioned above. In the one side of corrugated hose 20$b$, inner casing tube 5 is inserted, the other side is connected with the housing of the feeding unit if needed, by a tube 26 indicated.

Figure 6:
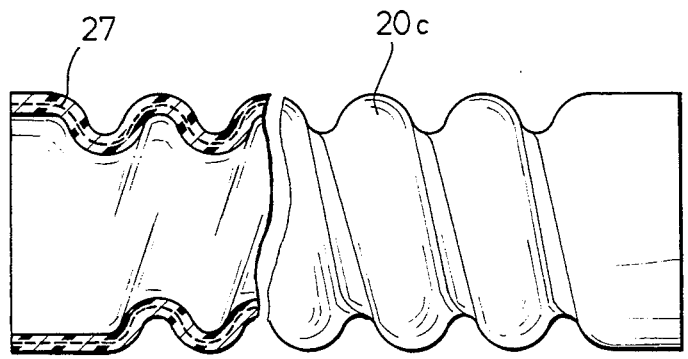

FIG. 6 shows an additional length compensating element 20$c$, which also consists of a corrugated hose, of plastic in this case, into which threads or a fabric 27 are embedded as reinforcement or to prevent radial extension.

Figure 7:
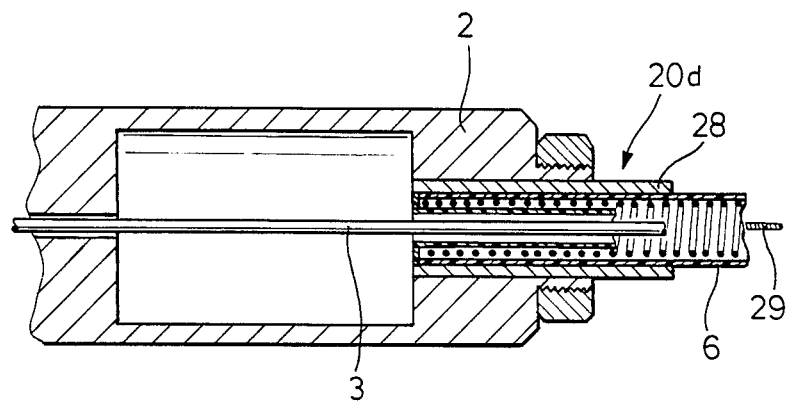
FIG. 7 shows an additional practical example of a length compensating element for a casing tube, which serves mainly as a buckling protection for the light guide fiber.

FIG. 7 shows a length compensating element 20$d$, in this case for the outer casing tube 6. The length compensating element 20$d$ has a telescope sleeve 28, which is anchored in the end of feeding unit 2 and surrounds outer casing tube 6 in a smooth line. This outer casing tube 6 can be moved in telescoping sleeve 28 so that longitudinal changes between light guide fiber 3 and casing tube 6 can be compensated. To prevent a pulling out of casing tube 6 from the telescoping sleeve, suitable shoulders are provided or a steel cable 29 is laid along casing tube 6, with one end attached at the feeding unit and the other end at the exposed end of light guide fiber 3 not shown here. The length of steel cable 29 corresponds to the length of the light guide fiber between the two fastening points.

In the foregoing specification, the invention has been described with reference to specific exemplary embodiments thereof It will, however, be evident that various modifications and changes may be made thereunto without departing from the broader spirit and scope of the invention as set forth in the appended claims. The specification and drawings are, accordingly, to be regarded in an illustrative rather than in a restrictive sense.

What is claimed is:

1. A light guide, particularly for a medical instrument, comprising a light guide fiber, a casing that surrounds the light guide fiber at a distance therefrom and comprising at least a casing tube and further comprising a feeding unit at one end of the light guide for the feeding of light radiation into the light guide fiber, one end of the light guide fiber and the casing tube being mounted in the feeding unit and the other end of the light guide fiber mounted in the casing tube, and further comprising length compensating means, which can change its length axially, but is largely not expandable radially, disposed in and forming a part of the casing tube for compensating for differences in length of said light guide fiber and casing tube.

2. The light guide recited in claim 1, wherein the length compensating means comprises an elastic tube surrounded by spiral spring means.

3. The light guide recited in claim 1, wherein the length compensating means comprises corrugated hose means.

4. The light guide recited in claim 3, wherein the corrugated hose means comprises metal.

5. The light guide recited in claim 3, wherein the corrugated hose comprises plastic, having fabric or threads embedded therein.

6. The light guide recited in claim 1, wherein the length compensating means comprises telescoping means including a telescoping sleeve having said casing tube of the casing slidable therein.

* * * * *